US006480276B1

United States Patent
Jiang (10) Patent No.: US 6,480,276 B1
(45) Date of Patent: Nov. 12, 2002

(54) ENHANCED PHOTON-MIGRATION METHODS FOR PARTICLE SIZING IN CONCENTRATED SUSPENSIONS

(75) Inventor: Huabei Jiang, Clemson, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 09/615,914

(22) Filed: Jul. 13, 2000

Related U.S. Application Data (60) Provisional application No. 60/143,449, filed on Jul. 13, 1999.

(51) Int. Cl.[7] .............................................. G01N 15/02
(52) U.S. Cl. ....................... 356/336; 356/337; 356/339; 250/575
(58) Field of Search ................................ 356/336–343, 356/73, 301; 250/574, 575; 73/61.41, 602

(56) References Cited

U.S. PATENT DOCUMENTS

| | | | |
|---|---|---|---|
| 4,245,909 A | 1/1981 | Loos | |
| 4,338,030 A | 7/1982 | Loos | |
| 4,361,403 A | 11/1982 | Loos | |
| 4,473,296 A | 9/1984 | Shofner et al. | |
| 4,541,719 A | 9/1985 | Wyatt | |
| 4,676,641 A | 6/1987 | Bott | |
| 4,779,003 A | 10/1988 | Tatsuno | |
| 4,781,460 A | 11/1988 | Bott | |
| 4,830,494 A | 5/1989 | Ishikawa et al. | |
| 5,007,737 A | 4/1991 | Hirleman, Jr. | |
| 5,024,526 A * | 6/1991 | Von Redwitz | 356/339 |
| 5,064,765 A | 11/1991 | Karasikov et al. | |
| 5,121,629 A * | 6/1992 | Alba | 73/61.41 |
| 5,164,604 A | 11/1992 | Blair et al. | |
| 5,164,787 A | 11/1992 | Igushi et al. | |
| 5,185,641 A | 2/1993 | Igushi et al. | |
| 5,245,200 A | 9/1993 | Fladda | |
| 5,286,452 A | 2/1994 | Hansen | |
| 5,309,215 A | 5/1994 | Schumann | |
| 5,369,037 A | 11/1994 | Hansen | |
| 5,383,024 A * | 1/1995 | Maxey et al. | 356/336 |
| 5,438,408 A | 8/1995 | Weichert et al. | |
| 5,452,602 A | 9/1995 | Astakhov et al. | |
| 5,455,675 A | 10/1995 | Witt et al. | |
| 5,576,827 A | 11/1996 | Strickland et al. | |
| 5,594,544 A | 1/1997 | Horiuchi et al. | |
| 5,650,847 A | 7/1997 | Maltsev et al. | |
| 5,751,423 A | 5/1998 | Traina et al. | |
| 5,818,583 A | 10/1998 | Sevick-Muraca et al. | |
| 5,831,730 A | 11/1998 | Traina et al. | |
| 5,835,211 A | 11/1998 | Wells et al. | |
| 5,861,951 A | 1/1999 | Uesugi et al. | |
| 5,878,160 A | 3/1999 | Horiuchi et al. | |
| 5,940,177 A | 8/1999 | Esser et al. | |
| 5,973,779 A * | 10/1999 | Ansari et al. | 356/342 |
| 6,219,138 B1 * | 4/2001 | Swanson et al. | 356/336 |

OTHER PUBLICATIONS

Jiang, "Particle sizing in concentrated suspensions by use of steady–state, continuous–wave photon–migration techniques," *Optics Letters*, vo. 23, No. 5, Mar. 1, 1998, pp 394–396.

Jiang, "Enhanced Photo–Migration Methods for Particle Sizing in Concentrated Suspensions", *AIChE Journal*, Aug. 1998, vol. 44, No. 8, pp 1740–1744.

Sevick–Muraca, et al, "Photon–Migration Measurement of Latex Size Distribution in Concentrated Suspensions," AIChE Journal, Mar., 1997, vol. 43, No. 3, pp 655–664.

* cited by examiner

Primary Examiner—Frank G. Font
Assistant Examiner—Sang H. Nguyen
(74) Attorney, Agent, or Firm—Dority & Manning, PA (57) ABSTRACT

A method and apparatus for determining particle size distribution in undiluted suspensions using spectral measurements of transport-scattering co-efficients using continuous photon-migration techniques is provided. Particle size distribution for concentrated suspensions is determined by a regularized inverse algorithm and may be obtained without a priori distribution function assumptions.

7 Claims, 7 Drawing Sheets

ENHANCED PHOTON-MIGRATION METHODS FOR PARTICLE SIZING IN CONCENTRATED SUSPENSIONS

RELATED APPLICATIONS

This application claims the benefit of U.S. Provisional Application No. 60/143,449 filed on Jul. 13, 1999, and which is incorporated herein by reference in its entirety.

FIELD OF THE INVENTION

This invention relates to an apparatus and process for the determination of particle size data such as particle size and density.

BACKGROUND OF THE INVENTION

Particulate suspensions are common in a variety of industries including ceramics, metals, foods, medical research, pharmaceuticals, pesticides, cosmetics, and paints and pigments. The two major categories of control parameters for the processing of particle/fluid suspensions are particle physics and interparticle chemistry Funk, J. E., and D. R. Dinger, Predictive Process Control of Crowded Particulate Suspensions Applied to Ceramic Manufacturing, Kluwer, Boston (1994). One of the most important particle physics parameters to measure and control is the particle size distribution (PSD) of the powder. In suspensions and in powder processing in general, PSD affects many process and product properties including particle packing densities, the nature and number of interparticle contacts within a compact, the interparticle porosity and pore size distribution in a compact, suspension rheology and viscosity, drying and firing behavior, and other related properties.

Control of the PSD of powders in a body is effectively complete when the powders have been poured into the mixing device. Frequently, fluctuating body properties caused by variations in powder PSDs are adjusted using additive chemicals, that is, body property variations caused by one parameter (particle physics) are corrected by adjusting the other parameter (interparticle chemistry). Adjusting one control parameter to overcome variations caused by another is not advisable but common. To successfully process any particulate system, it is important that particle physics variations be controlled by adjustments to particle physics. Interparticle chemistry imbalances can then be controlled by adjustments to chemistry and the whole suspension can function as designed. To do this, one must be able to quickly and accurately measure the complete PSD of all constituent powders used in a batch formulation.

A major problem with all of the common particle size analysis techniques available today, including sedimentation, Coulter principle, dynamic light scattering, and turbidity measurement is the requirement of extremely dilute suspensions. These techniques cannot be used at normal suspension densities and require careful sampling followed by dilution and further sampling to achieve the small, highly dilute samples required for the analyses. In addition, these techniques often require calibration on the process stream they are intended to monitor.

Representative examples of prior art particle analysis systems include U.S. Pat. Nos. 5,818,583; 5,940,177; 5,861, 951; 5,835,211; 5,831,730; 5,751,423; 5,650,847; 5,576, 827; 5,455,675; 5,452,602; 5,438,408; 5,369,037; 5,309, 215; 5,286,452; 5,245,200; 5,185,641; 5,164,787; 5,164, 604; 5,105,093; 5,064,765; 5,007,737; 4,830,494; 4,781, 460; 4,779,003; 4,676,641; 4,541,719; 4,473,296; 4,361, 403; 4,338,030; and 4,245,909. The U.S. Patents listed above are incorporated herein by reference in their entirety.

To overcome the problems associated with the present techniques for particle sizing, a new optical method based on frequency-domain measurements of photon-migration in scattering suspensions has recently been proposed as set forth in applicant's recent publications Jiang, H., G. Marquez, and L V. Wang, "Particle Sizing in Concentrated Suspensions Using Steady-State, Continuous-Wave Photon Migration Techniques," Opt. Lett., 23, 394 (1998) and Jiang, H., J. Pierce, 1. Kao, and E. Sevick-Muraca, "Measurement of Particle-Size Distribution and Volume Fraction in Concentrated Suspensions with Photon Migration Techniques," Appl. Opt., 36, 3310 (1997), and which are both incorporated herein in their entirety by reference. Because the frequency-domain technique depends upon multiply scattered light, it is particularly suitable for non-dilute suspensions and has great potential for on-line process monitoring. In addition, transport scattering and absorption coefficients can be measured separately. Wavelength-dependent absorbances do not distort scattering measurements; hence, the technique does not require calibrations on the suspensions.

However, initial findings make use of a frequency-domain Ti:Sapphire laser system, which does not provide a light beam having a wide range of spectra. Furthermore, the procedures for optical data collection were relatively slow since measurements at multiple wavelengths were needed.

The present invention demonstrates particle sizing in concentrated $TiO_2$ suspensions, using continuous wave-based photon-migration techniques. Compared with the frequency domain techniques, this method allows faster and simpler measurements of optical properties in a scattering medium with the same accuracy as the frequency-domain techniques. Background details on the methodology and underlying theory may be found in Wang, L., and S. L. Jacques, "Use of a Laser Beam with an Oblique Angle of Incidence to Measure the Reduced Scattering Coefficient of a Turbid Medium." Appl. Opt., 34, 2362 (1995); Nichols, M., E. Hull, and T. Foster, "Design and Testing of a White-Light, Steady State Diffuse Reflectance Spectrometer for Determination of Optical Properties of Highly Scattering Systems," Appl. Opt., 36, 93 (1997); Lin, S. P., L Wang, S. L Jacques, and F. K. Tittel, "Measurement of Tissue Optical Properties by the Use of Oblique—Incidence Optical Fiber Reflectometry." Appl. Opt., 36, 136 (1997); and Kienle, A., L Ulge, M. S. Patterson, R. Hibst. R. Steiner, and B. C. Wilson, "Spatially Resolved Absolute Diffuse Reflectance Measurements for Non-Invasive Determination of the Optical Scattering and Absorption Coefficients of Biological Tissue," Appl. Opt., 35, 2304 (1996); the above references being incorporated herein in their entirety. The continuous wave-based system is more economical to supply and operate than its frequency-domain counterpart and offers additional advantages as set forth below.

Photon-migration measurements monitor the characteristics of multiply scattered light as it consecutively scatters from particle to particle. Any fluid or solid material in which the scattering effect of reflected or transmitted light may be determined and may be used to advantage with the present process and methodology and include solutions of a wide range of particle concentration along with gaseous samples, tissue evaluations, and other samples of solids, liquids, or gases. Through the spectral measurement of isotropic or reduced scattering coefficient of a sample, such as tissue, the PSD can be recovered using a regularized inverse algorithm. The photon-migration technique is particularly useful in two aspects: it can analyze particles in dense suspensions without dilution since it depends on multiply scattered light and is thus suitable for on-line process monitoring; and, transport scattering and absorption coefficients of the suspensions can be measured separately, so that wavelength-dependent absorbances do not distort scattering measurements. This enables accurate solution of the inverse problem for determining PSD.

In accordance with this invention, it is possible to use continuous wave-based photon-migration measurements for determination of the transport-scattering coefficients. Useful applications of an inverse algorithm for reconstructing PSD in concentrated suspensions is also disclosed. Using a regularized inverse algorithm, the reconstructed PSD's of $TiO_2$, suspensions with three different concentrations are set forth. The results are in excellent agreement with the size distribution measured with x-ray sedimentation. These reconstructions of PSDs may be obtained both with and without a priori distribution function assumptions.

The continuous wave based photon migration technique depends on a source of radiation capable of being scattered as a result of contact with particles in a suspension or solution. This invention discloses that the visible spectrum in the range of 400 to 800 nm yields desired result. While it is convenient to use the visible spectrum, the invention anticipates that a full range of radiation wavelengths that can be scattered by contact with material in suspension or solution may be employed. Depending upon the nature of the material to be analyzed, desired wavelengths of radiation may be selected.

DETAILED DESCRIPTION OF A PREFERRED EMBODIMENT

The continuous-wave photon-migration techniques involve launching time-independent light into a highly-scattering medium and measuring the relative intensity of reflected or transmitted light. In highly scattering media, the propagation of light can be described by the well-known time-independent diffusion equation Duderstadt, J. J, and L. 1. Hamilton, Nuclear Reactor Analysis, Wiley, N.Y. (1976). By fitting measured relative intensity of reflected or transmitted light to the solution of the diffusion equation under the condition of semi-infinite sample geometry, the spectral measurements of the transport scattering and absorption coefficients are obtained. The spectral measurements can be achieved by a simple fitting procedure (Nichols et al., 1997), or by an oblique incident reflectometry (Wang and Jacques, 1995; Lin et al., 1997). The data set forth below were collected by the latter approach. Some of the data have been previously reported in Applicant's paper entitled "Enhanced Photon-Migration Methods for Particle Sizing in Concentrated Suspension" in *Particle Tech. And Fluidization*, Vol. 44, No. 8, pp. 1740–1744, 1998 which is incorporated herein by reference in its entirety.

Figure 1:
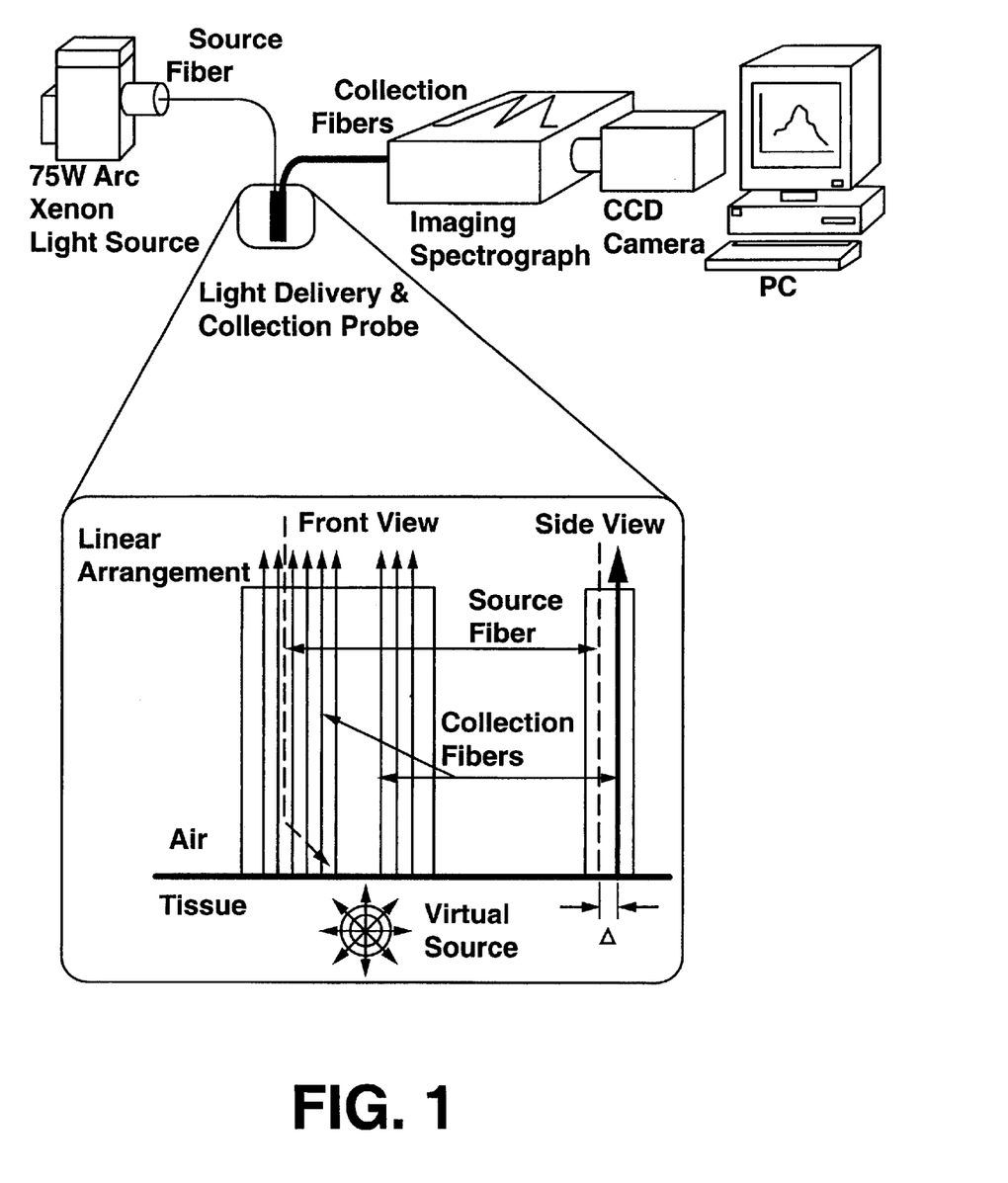
FIG. 1 is a schematic view of the apparatus and process for determining,and calculating the concentration data and particle size distribution data in accordance with this invention.

The experimental system used in this study is schematically shown in FIG. 1 in which white light from a 75-W Xenon Arc Lamp was delivered, and the diffuse reflectance was measured as a function of source-detector distance by a fiber-optic probe. The source fiber was oriented at a 45° angle of incidence, and the nine collection fibers, arranged in a linear array, collected the diffuse reflectance. To correct for slight variations in collection efficiency from one detection fiber to the next, a correction factor was calculated for each fiber based on a calibration procedure using standard phantoms. The detection system was composed of an imaging spectrograph, a CCD camera, and a PC to automatically record the spectrum of the collected light through the wavelength range of 400–800 nm. The spectral resolution of the measurements was 0.50 nm.

Monochromatic light is not suitable for applications taught in this invention. Although the spectrum of visible radiation is continuous, in this invention components of the spectrum were separated in the detection system at 0.50 nm. Results confirm that the continuous wave illumination produces a more stable result compared with frequency domain or time dependent methodologies. An illumination comprising at least three identifiable wavelengths is required for the application of essential equations. Having a larger number of identifiable wavelengths is preferred in that accuracy and processing time are believed to be improved.

Figure 2:
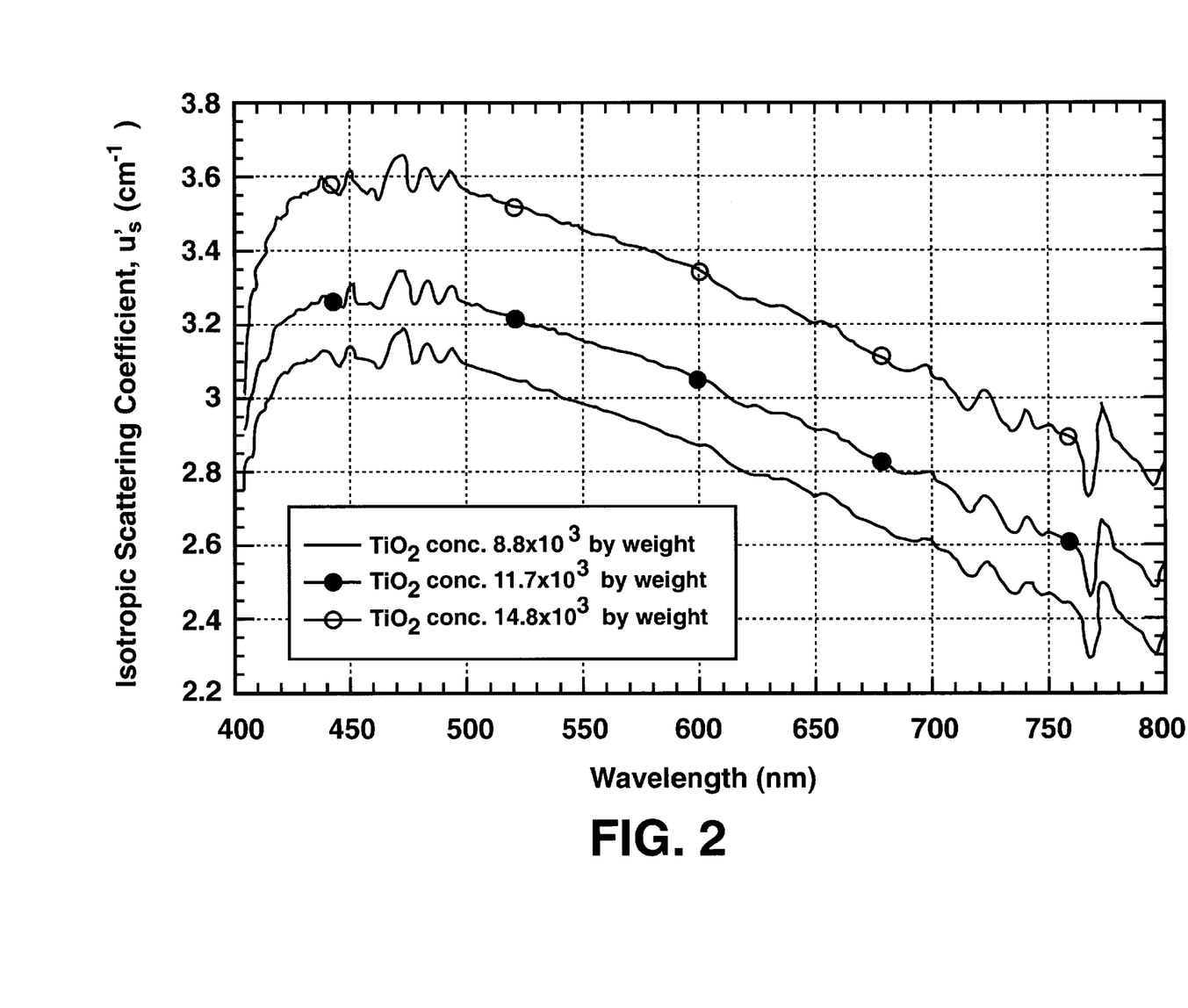
FIG. 2 is a graphical representation of transport-scattering spectra versus wavelength as determined by oblique incident reflectometry obtained with the apparatus of FIG. 1.

The fiber probe was placed on the surface of the concentrated suspensions. An exposed x-ray film was attached to the top of the suspensions to approximate a matched boundary condition for diffusion theory. Four measurements were performed with the probe oriented at 0°, 30°, 60°, and 90° with respect to an arbitrary reference orientation. The transport-scattering spectra were evaluated for each diffuse reflectance measurement, and the results were averaged. The concentrated suspensions were a mixture of $TiO_2$ India ink, and polyacrylamide gel that produced $TiO_2$, concentration values of $8.8 \times 10^{-3}$, $11.7 \times 10^{-3}$ and $14.6 \times 10^{-3}$ Wt. % respectively. Note that while the addition of the India ink is not necessary for the purpose of particle sizing, an appreciable absorption can exist in particle suspensions. The photon-migration techniques used are capable of separately measuring scattering and absorption coefficients; thus, wavelength-dependent absorbances did not distort the scattering measurements. The mixture was poured into a plastic container 8 cm in diameter and 6 cm in height before gelling. FIG. 2 presents the transport-scattering spectra measured for the $TiO_2$, suspensions with three different concentrations. The standard deviations between the source fiber orientation angles for each concentration are 0.16, 0.25, and 0.37 for the concentrations of $8.8 \times 10^{-3}$, $11.7 \times 10^{-3}$, and $14.6 \times 10^{-3}$ Wt. %, respectively.

The inverse algorithm used casts particle sizing as an optimization problem in which the optimization parameters are fully variable, discretely classified PSDs or coefficients in a probability function (such as a log normal or Gaussian distribution function using a priori assumptions. The details of the inverse algorithm have been given in applicant's earlier publications of cited above and Sevick-Muraca, E., J. Pierce, H. Jiang, and J. Kao, "Photon-Migration Measurement of Latex Size Distribution in Concentrated Suspensions," AIChE 1., 43, 655 (1997) incorporated herein by reference and are summarized below.

It is known that PSD in a multiply scattering medium is correlated with the transport-scattering coefficient of the medium by the following relationship as described in Van de Hulst, H., Light Scattering by Small Particles, Dover, N.Y. (1983) and Bohren. G. F., and D. R. Hoffman, Absorption and Scattering of Light by Small Particles. Wiley. N.Y. (1983) as set forth in equation 1:

$$(1-g)\mu_s(\lambda) = \mu'_s(\lambda) \qquad (1)$$

$$= \int_0^\infty \frac{3Q_{scat}(x, n, \lambda)[1 - g(x, n, \lambda)]}{2x} \phi f(x) dx$$

where $(1-g)\mu$, is the transport-scattering coefficient, g is the mean cosine of the scattering angle from a single particle, $Q_{scat}$ is the scattering efficiency, n is the refractive index of the medium and $\lambda$ is the wavelength-of light, f(x) (x is the diameter of the particles) is the particle volume size distribution and $\phi$ is the total volume fraction of the particles. Both quantities of g and $Q_{scat}$ can be computed using the Mie theory (Bohren and Hoffman, 1983). To use Eq. 1 correctly, it is assumed that no particle-particle interaction exists and that it applies only to spherical particles.

In the prior art, f(x) of Eq. 1 requires an a priori assumption regarding the particle size distribution such as a log normal or gaussian distribution. The present invention teaches that although a variable must be provided, no need exists for the variable to be dependent upon any a priori assumption regarding particle size distribution. Thus, the inverse problem becomes to find the particle size distribution, f(x), and the volume fraction, $\phi$ from measurements of the transport-scattering coefficients at multiple wavelengths. Using regularized optimization methods, we obtain the following system of equations leading to the inverse problem solution (Jiang et al., 1997, 1998; Sevick-Muraca et al., 1997):

$$(J^T J + \alpha I)\Delta \zeta = J^T[(\mu'_s)^o - (\mu'_s)^c] \qquad (2)$$

where the Jacobian matrix T represents the sensitivity of transport-scattering coefficients measured at multiple wavelengths, the elements of which are numerically computed using Eq. 1. I is the identity matrix and $\alpha$ may be a scalar or a diagonal matrix. The vectors, $(\mu'_s)^o$ and $(\mu'_s)^c$ contain the observed and computed values of transport-scattering coefficients at the wavelengths of interest.

The significance of freedom from dependence on an a priori assumption regarding particle size distribution is also reflected in the solution of the equation for a log normal distribution. In the log normal equation both "a" and "b" or unknowns which must be determined if this distribution is assumed. The present teaching eliminates the requirement for a priori assumption of a distribution and thereby eliminates the need to solve for "a" and "b".

The numbers of the elements of $\Delta \zeta$ and T depend on whether we use a priori knowledge about the number of modes and their size distribution functions or not. If we use a log normal distribution in this study for $TiO_2$, suspensions, Crow, E. L., and K. Shimizu. Log normal Distributions, Marcel Dekker, New York (1988).

$$f(x) = \exp[-(\ln x - a)^2/2b^2]/\sqrt{2\pi}bx$$

where parameters a and b denote the mean and variance of the distribution, respectively, then the number of the elements of $\Delta \zeta$ is three (we choose $\phi$ as the third parameter) and the number of elements of T is M×3, where M is the number of wavelengths; if we do not use a priori knowledge about the number of modes and their size distribution functions, then the numbers of the elements of $\Delta \zeta$ and T become N and M×N, respectively, where N is the number of intervals that are equally discretized for the product $\phi f(x)$ (Sevick-Muraca et al., 1997).

Thus, the basic method for determining f(x) and $\phi$ is to measure the transport-scattering coefficient of the suspensions at multiple wavelengths. Then the particle sizing task is to make estimates (which are updated and improved through the solution of Eq. 2) of parameters a, b, and c or discretized f(x) and $\phi$ that are required for the measured scattering coefficients to be sustained. Since the matrix $J^T J$ is known to be ill-conditioned, a way to regularize or stabilize the decomposition of $J^T J$ is needed. We used a hybrid technique that synthesizes the standard Marquardt and Tikhonov regularization schemes (Jiang et al., 1997, 1998; Sevick-Muraca et al., 1997).

EXAMPLE 1

We have used the above described inverse algorithm to reconstruct the particle size distributions for dense $TiO_2$ suspensions with three different concentrations. To reconstruct a typical PSD shown below, only a few seconds were needed with a SunSparc 5 workstation. It has been found that the inversion results were not very sensitive to the choices of the uniform initial estimates of the discretized size distribution or parameters in the known probability distribution function, which were up to 100% greater than the true values, depending of course on the optical property measurements.

Figure 3:
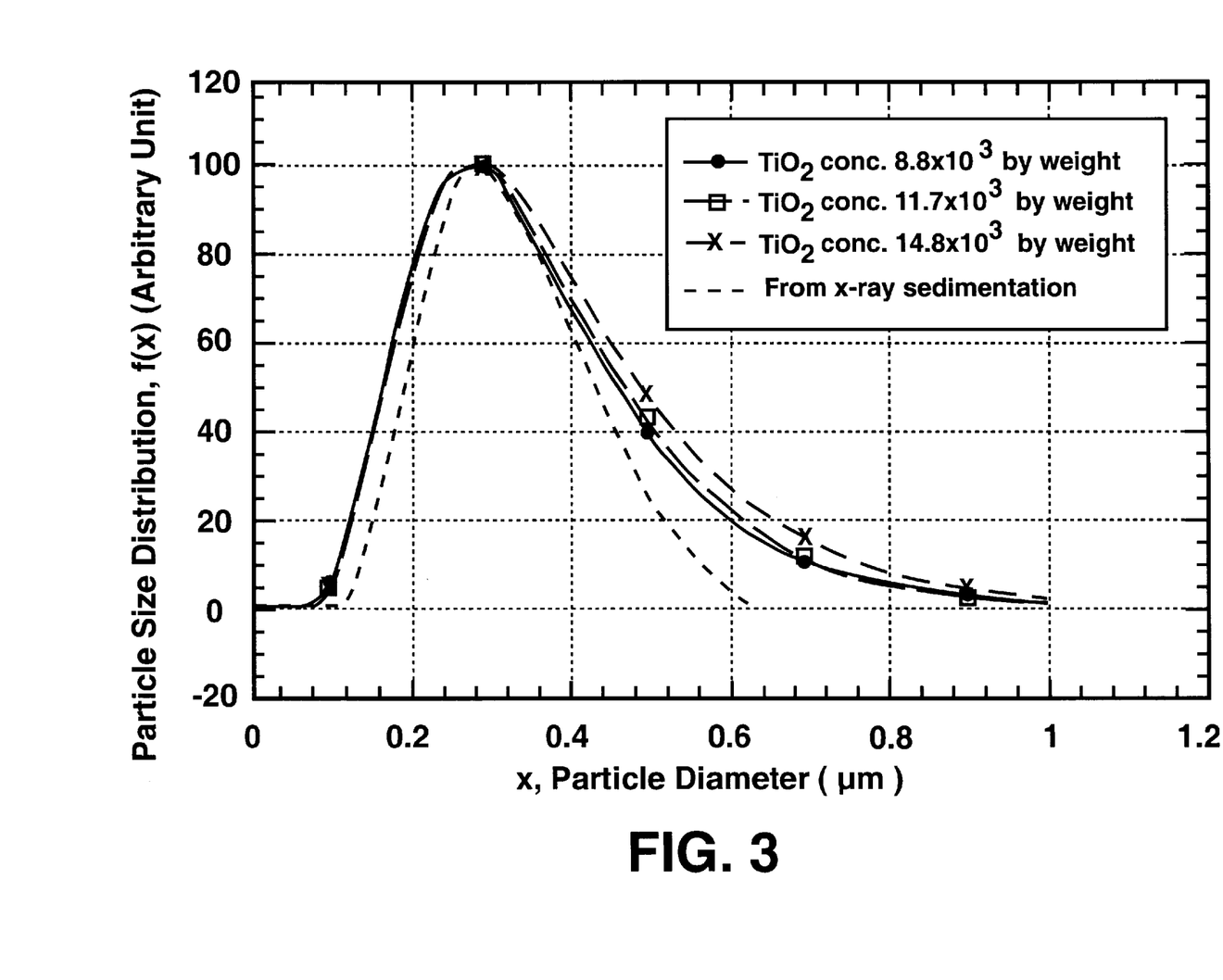
FIG. 3 is graphic representation of particle size distribution as a function of diameter for $TiO_2$ using the apparatus and process of FIG. 1.

FIG. 3 shows the particle size distributions recovered for all three $TiO_2$ suspensions with a priori log normal distribution function assumption. The lines with symbols denote the reconstructed values from the photon-migration measurements and the dashed line represents the size distribution obtained from the sedimentation measurement for comparison. The figure shows that an excellent agreement between our results and those yielded by the sedimentation has been reached. The relative error between the computed and the measured transport-scattering coefficients at each iteration, defined as:

$$\left(\sqrt{\sum_{i=1}^{M} [(\mu'_s)^o_i - (\mu'_s)^c_i]^2}\right)_{J \geq 1} \bigg/ \left(\sqrt{\sum_{i=1}^{M} [(\mu'_s)^o_i - (\mu'_s)^c_i]^2}\right)_{J=0}$$

Figure 4:
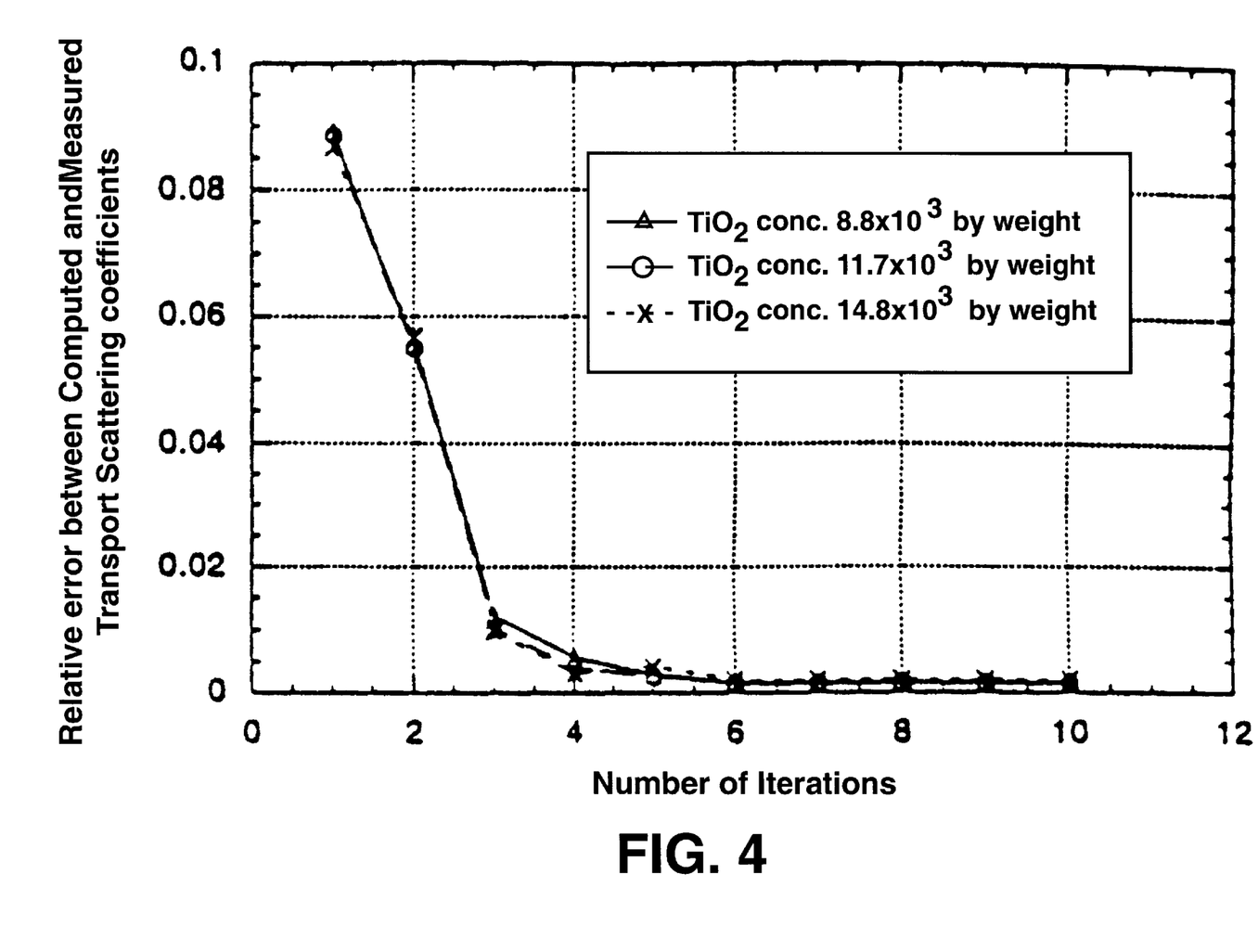
FIG. 4 is a graphical representation of error guide use of the results obtained and set forth in FIG. 3.

M is the number of wavelengths and J is the number of iterations J=0 denotes that the calculation is performed before the iterative procedure begins), as shown in FIG. 4. In this case, the reconstructed volume fractions ($\phi$) are 0.92%, 1.24%, and 1.61%, respectively.

Figure 5:
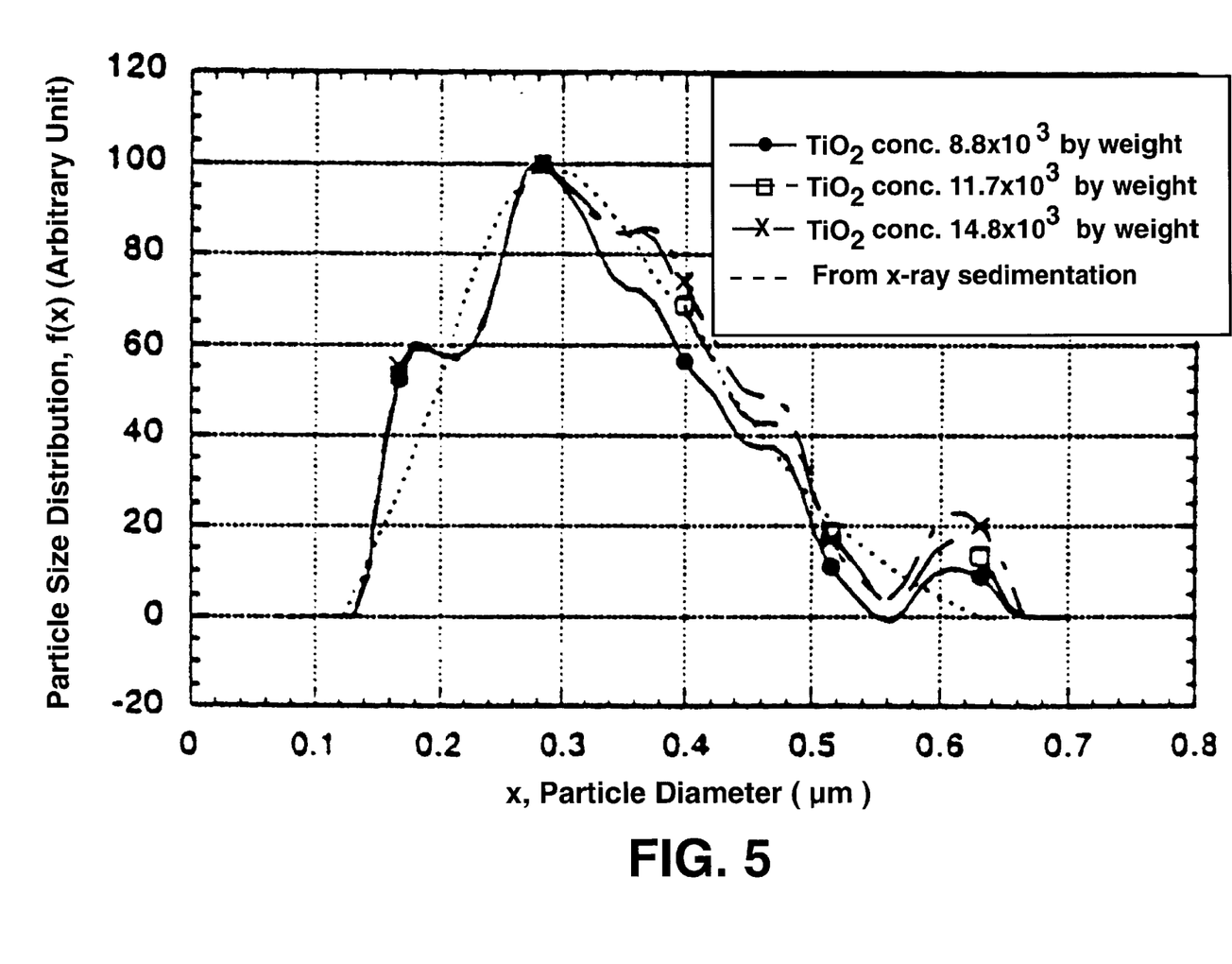
FIG. 5 is a graphic representation of particle size distribution as a function of diameter for $TiO_2$ samples using no a priori distribution function assumptions.
Figure 6:
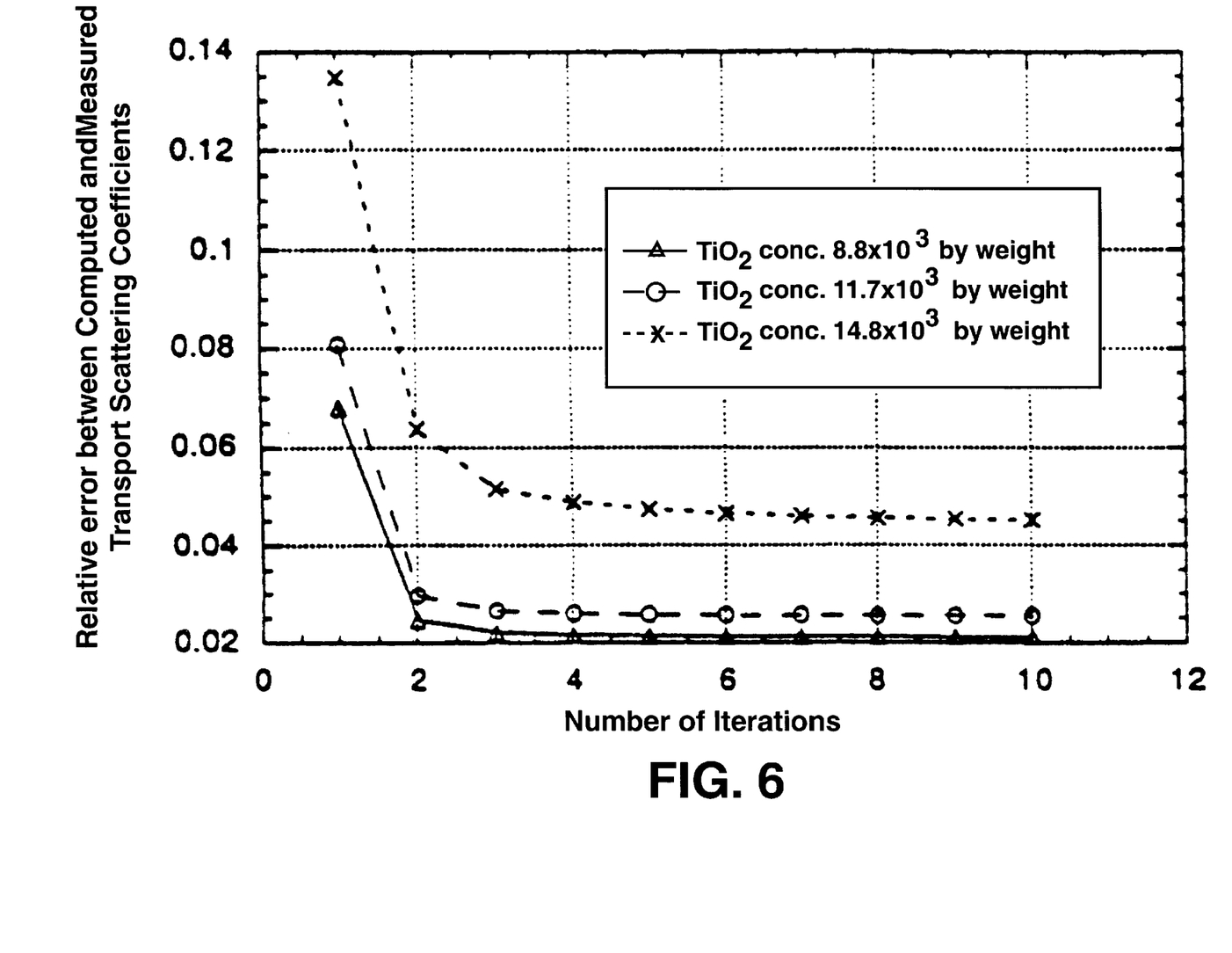
FIG. 6 is a graphic representation of the relative error between computed scattering coefficients versus the number of iterations of the algorithm.

FIG. 5 presents the particle size distributions recovered for all three $TiO_2$, suspensions where no a priori distribution function assumption was used. Again, a very good agreement has been achieved between these results and x-ray sedimentation. FIG. 6 gives the relative error of the inverse solution in this case. The recovered volume fractions ($\phi$) are 0.90%, 1.21%, and 1.59%, respectively.

EXAMPLE 2

The equipment and apparatus described in referenced to Example 1 was used to determine particle size distribution for potassium chloride (KCl) solutions, a common compound found in many commercial fertilizers. A saturated solution of KCl was prepared by adding excess KCl to a volume of distilled water in a glass beaker. The temperature of the solution to return to room temperature following the additional of excess salt is evidenced by undissolved salt in the beaker. The density of the KCl solution at the ambient temperature was 1.22 gm/ml.

The saturated KCl solution was used to suspend a 35 percent solution by weight of a KCl study material. The suspension was constantly stirred using a magnetic stirrer. The unmodulated light source described above was directed to the surface of the KCl suspension solution. Particles of the suspended KCl scattered the incident light as the light illuminated the solution and the particles. A plurality of the fiber optic cables were positioned within the glass container to collect the multiply scattered light. The optical cables are used to transfer the received light to a charged couple device in which a prism structure separates the light into groups of different wavelengths and which then converts the transmitted light to an electron value to allow a score unit count by wavelength of light. The input data from each optic fiber probe for each wavelength is normalized to yield a distribution curve for each wavelength. The optical properties as a result of this analysis include the light absorption coefficient and the light scattering coefficient which may be plotted to yield a respective curve of absorption and light scattering. The CCD is connected to a personal computer which applies the algorithm referenced above to the solution of a series of equations that includes applications of known correlations between scattering and absorption. The application of the algorithm is a reiterative process and yields the particle size distribution of the KCl particles suspended in the saturated solution of KCl. The reiterative curve fitting process continues until a stable curve is identified and based upon the scattering pattern.

Figure 7:
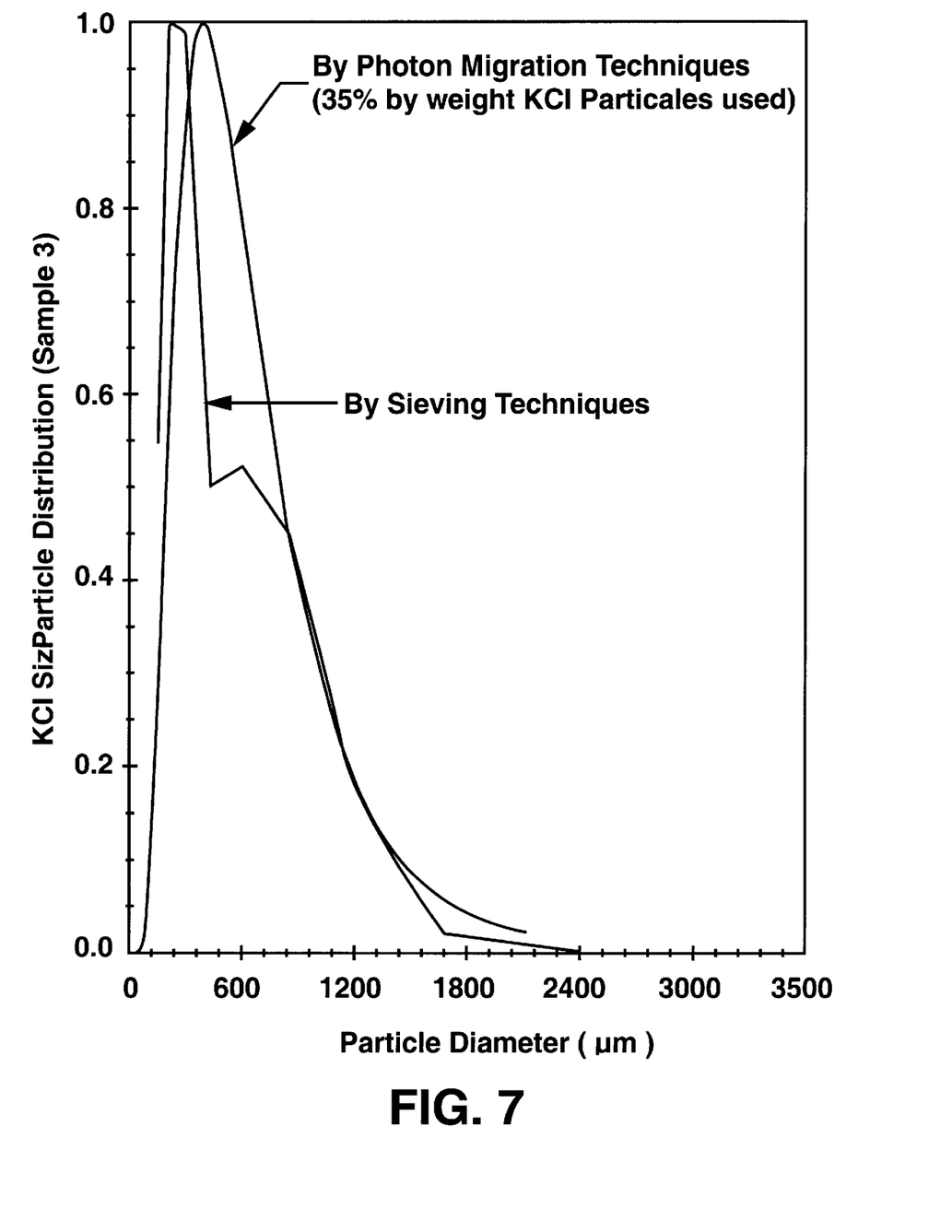
FIG. 7 is a graphic representation of particle size distribution as a function of diameter for KCl using the apparatus and process of FIG. 1.

As set forth in FIG. 7, a comparison of particle size based upon the photon-migration techniques of the present invention is compared to the manual calculation of particle size based upon sieving techniques. As seen in reference to FIG. 7, the photon-migration technique provides accurate measurement of the particle size and produces the measurements in real time as opposed to the time-consuming manual calculation of particle size used as the control measurement value.

The above process is suitable for diverse applications such as particle measurements with respect to ink formulations, paint formulations, concrete mixtures, and for evaluating density or other changes with respect to plant or animal tissue.

DISCUSSION AND CONCLUSIONS

The results presented in the examples above clearly indicate that one may determine particle size distribution in concentrated suspensions with and without a priori distribution function assumptions using continuous-wave photon-migration measurements. Since the optical property measurements occurred at wavelengths between 400 nm and 800 nm, having obtained PSD in concentrated suspension without a priori distribution function assumption for the first time. This approach allows us to reconstruct PSD with an arbitrary shape. This is an important advancement of our approach because we may not have such a priori information in many practical situations. In addition, the inverse solution procedure in our reconstruction was quite stable, whereas an unstable solution procedure has been experienced using frequency-domain photon-migration techniques (measurements at only 15 wavelengths were made (Jiang et al., 1997; Sevick-Muraca et al., 1997). This is clearly evidenced by the relative error or converging rate shown in FIGS. 4 and 6.

From FIGS. 3 and 5, one can observe that the increase of the particle concentration from $8.8 \times 10^{-1}$ to $14.6 \times 10^{-3}$ by weight does not make significant impact on the recovery of PSD. Although we do see a larger relative error between the computed and the measured transport scattering coefficients for the case of higher particle concentration in FIG. 6, this does not affect the reconstruction of PSD significantly because the error shown is only relative. Clearly this observation should be restricted to the particle concentrations used in this study. The actual limits of the particle concentration for which our approach is applicable warrant future study. It is also interesting to note that, while the shape of particles in $TiO_2$ suspensions is not perfectly spherical, the spherical particulate-based Mie theory still provides one with accurate results from the inverse algorithm. This could be due to the use of the hybrid regularization in the iterative optimization procedure, which provides a compensation mechanism for the geometrical discrepancy that occurs in the theory. In FIG. 3, some discrepancies are noted at longer wavelengths between the photon-migration results and those measured with x-ray sedimentation. It is believed that the discrepancies are due to the assumption of a priori log normal distribution function since these discrepancies did not exist when we did not use the a priori assumption (FIG. 5). While our solution employed 800 wavelength measurements, the minimum number or choice of appropriate wavelengths required for a successful and optimal inverse solution may vary and may differ further based upon the sample material being evaluated.

In summary, the present invention makes use of continuous-wave photon-migration measurements of transport-scattering for particle sizing in concentrated suspensions. The results show that fast, simple continuous-wave photon-migration measurements in a wide range of wavelengths, coupled with an efficient inverse algorithm, can provide PSD of concentrated suspensions in a matter of seconds. This indicates its potential for on-line process monitoring and is particularly useful in that a priori assumptions are not required to obtain accurate, rapid measurements.

What is claimed is:

1. A process for determining particle size distribution of a suspension comprising the following steps:

exposing a suspension of particles to an uninterrupted continuous wave source of light;

collecting a scattered light;

analyzing the scattered light into spectral components of said scattered light;

transmitting the spectral components of the scattered light to a microprocessor;

calculating a relative intensity of reflected light within the suspension;

calculating a relative intensity of transmitted light within the suspension;

obtaining spectral measurements of a transport scattering coefficient by fitting measured relative intensity of the reflected or the transmitted light;

obtaining the spectral measures of the absorption coefficient by fitting measured relative intensity of one of said reflected or said transmitted light;

using an algorithm that is free of an a priori assumption as to the distribution of particle size to reconstruct the particle size distribution of the suspension.

2. The process according to claim 1 wherein the algorithm is a regularized, inverse algorithm.

3. The process according to claim 1 wherein the light source emits light in a visible spectrum.

4. The process according to claim 3 wherein the light source illumination is in a range of about 400 nm to about 800 nm.

5. The process according to claim 1 wherein the light source provides at least three different wavelengths of continuous electromagnetic radiation.

6. The process according to claim 1 wherein the step of collecting the scattered light further defines collecting the scattered light using fiber optic probes.

7. The process according to claim 1 wherein the light source further comprises white light.

* * * * *